United States Patent [19]

Kock et al.

[11] Patent Number: 5,429,942
[45] Date of Patent: Jul. 4, 1995

[54] BIOLOGICAL TREATMENT AND CULTIVATION OF MICROORGANISMS

[75] Inventors: Johan L. F. Kock; Alfred Botha, both of Bloemfontein, South Africa

[73] Assignee: Sasol Industries (Proprietary) Limited, Johannesburg, South Africa

[21] Appl. No.: 987,958

[22] Filed: Dec. 11, 1992

[30] Foreign Application Priority Data

Dec. 11, 1991 [ZA] South Africa ................. 91/9749

[51] Int. Cl.⁶ ........................... C12P 7/64; C12P 7/62
[52] U.S. Cl. ................................. 435/134; 435/135; 435/243; 435/254; 435/262.5; 435/264
[58] Field of Search ............ 435/134, 135, 243, 254.8, 435/262.5, 264, 931

[56] References Cited

U.S. PATENT DOCUMENTS

| | | | |
|---|---|---|---|
| 4,783,408 | 11/1988 | Suzuki et al. | 435/244 |
| 4,851,343 | 7/1989 | Herbert et al. | 435/134 |
| 4,857,329 | 8/1989 | Sako et al. | 514/558 |
| 4,868,001 | 9/1989 | Maruta | 426/623 |
| 4,870,011 | 9/1989 | Suzuki et al. | 435/134 |
| 4,916,066 | 4/1990 | Akimoto | 435/134 |
| 5,034,321 | 7/1991 | Nakajima et al. | 435/134 |
| 5,093,249 | 3/1992 | Nakajima et al. | 435/135 |
| 5,116,871 | 5/1992 | Horrobin et al. | 514/560 |

OTHER PUBLICATIONS

Moreton, R. S. (editor) "Single Cell Oil" Longman Scientific & Technical, Foreword.
Sinden, K. W. et al "Views and Comment" Enzyme Microb. Technol., (Feb. 1987), vol. 9, pp. 124–125.
"Estimation of Ammonia by the Indophenol Method". Butte, W. Rapid Method for the . . . Jour of Chroma. 15:695, pp. 142–145.
Dittmer, J. C. et al "Notes on Methodology" Jour of Lipid Research, vol. 5 (1961), pp. 126–127.
Folch, J. et al "A simple method for the isolation . . . " Jour of Biological Chem. (1957) 226, pp. 497–509.
Findlay, J. B. C. et al (editors) "Biological membranes . . . " IRL Press, Oxford, Washington, D.C. (1987), pp. 103–137.
Kendrick, A. et al "Lipids of selected molds . . " Lipids, vol. 27 No. 1 (1992), pp. 15–20.
Kock, J. L. F. et al "Short Communication . . . " Jour of General Microbiol, (1985) vol. 131, pp. 3393–3396.
Kreger-van Rij, N. J. W. "Methods for the isolation, maintenance . . . " The Yeasts, Elsevier Sci. Publishers B.V. Amsterdam (1984), pp. 40–104.
J. Sajbidor et al. "Influence of different carbon . . . " Biotechnology Letters, vol. 10 No. 5, 1988, pp. 347–350.
Patent Abstracts of Japan vol. 11 No. 192, Jun. 19, 1987.
Chemical Abstracts, vol. 102, 109, p. 402. Abstract #190–167–36x.

*Primary Examiner*—Douglas W. Robinson
*Assistant Examiner*—L. Blaine Lankford
*Attorney, Agent, or Firm*—Nixon & Vanderhye

[57] ABSTRACT

The invention discloses a method for producing a single cell oil containing gamma-linolenic acid characterized in that at least one microorganism of the order Mucorales preferably of the genus Mortierella, Actinomucor, Mucor, Rhizomucor or Rhizopus is cultured in a growth medium which is substantially starch and sugar free and which contains, as a carbon source material, at least one monocarboxylic acid of 2 to 5 carbon atoms, preferably acetic acid and recovering the oil from the resultant cultured microorganism biomass. The invention also relates to a method of treating the organic acid stream of the Fischer-Tropsch synthesis process to remove organic material therefrom.

9 Claims, No Drawings

BIOLOGICAL TREATMENT AND CULTIVATION OF MICROORGANISMS

FIELD OF THE INVENTION

This invention relates to a biological method of treating industrial effluent carrying carbon containing chemicals but which is substantially devoid of starches and sugars. It also relates to a method of cultivating microorganisms and to the recovery of valuable metabolites therefrom.

BACKGROUND OF THE INVENTION

Carbon based industrial chemical processes often give rise to aqueous effluent streams carrying a variety of carbon containing compounds. Thus, for example, it is known that the Synthol or Fischer-Tropsch Synthesis in which hydrocarbons, aliphatic alcohols, aldehydes and ketones are produced by the catalytic hydrogenations of carbon monoxide gives rise to an aqueous by-product or effluent stream, known as the "Fischer Tropsch organic acid stream". This stream typically contains between 1% and 3% of $C_2$ to $C_5$ monocarboxylic acids along with non-acidic chemicals such as ketones and aldehydes. This stream is conventionally treated by an activated sludge to strip the stream of its carbon content before recycling the purified water into the cooling circuit of the plant or running it into a river or the sea. The resultant biomass is either incinerated or may be disposed of as fertilizer.

In an unrelated field of technology it is known that certain microorganisms, known as oleaginous organisms, are capable of producing edible oils which oils have become known as Single Cell Oils or SCO's. [See for example the overview *SINGLE CELL OIL* edited by R. S. Moreton, Longman Scientific & Technical, 1988]

According to the work of Moreton referred to above, the first truly commercial SCO process is the one being carried out at the plant of Sturge Biochemicals in the United Kingdom at which a lipid rich in gamma linolenic acid [GLA; 6,9,12-octadecatrienoic acid] is produced. According to a report by K. W. Sinden of John and E. Sturge Limited [*Enzyme Microb. Technol.*, 1987 Vol. 9 p. 124-125] the microbial oil rich in GLA is produced by a Mucor sp. cultivated on a pure defined substrate based on glucose.

Gamma Linolenic Acid is a high value product which occurs in several natural products including breast milk, evening primrose oil, oats and other products. In the human and animal body it is converted to prostaglandin $E_1$, one of the important localised hormone type products regulating the body functions of the kidneys, liver, lungs, brain, nerve system and immune system. Products containing GLA are presently widely used in many parts of the world as a component of health food programs.

A large number of oleaginous organisms has been reported in the literature. The feedstock range on which such oleaginous organisms may be cultivated to produce lipids is quite diverse. According to literature reports such feedstock ranges from molasses, bananas, whey and potato starch to exotic carbon sources such as pentose, hexose sugars, disaccharides, glycerol, amino acids and ethanol. In general all such organisms are capable of assimilating glucose and other sugars while some are capable of assimilating starches. Reports on microorganisms capable of being cultivated on simpler forms of carbon-containing chemicals such as ethanol and glycerol do exist but relate to only a small number of specific SCO producing organisms.

It has been reported in Japanese patent application 81012479 that the microorganisms *Mucor javanicus, Rhizopus delemar* and *Aspergillus asumi* mut. *shirousamii* may be cultivated on waste water discharged from brewing, starch, rice, confectionary and cake producing or food processing factories. It will be readily appreciated that such waste water contains starch and/or sugars which are known nutrients for sustaining the growth of those microorganisms.

It has further been reported in European Patent Application 0269351 in the name of Lion Corporation that certain gamma-linolenic acid producing microorganisms may be cultured with fatty acids or fatty acid esters, more particularly fatty acids of between 8 and 22 carbon atoms as carbon source for the production of gamma-linolenic acid.

In European Patent Application 0155420 it is reported that microorganisms of the Mortierella genus may be cultured on glucose to produce a lipid rich in gamma-linolenic acid and that the efficiency of the culture is enhanced by the addition of acetic acid or an alkali metal acetate.

From the aforegoing it will be seen that the search for alternative producers of lipids rich in gamma-linolenic acid and for alternative feedstocks for use as a carbon source for such organisms is ongoing as it would clearly be advantageous to provide a process by which lipids rich in gamma-linolenic acid may be produced from simpler forms of carbon source materials.

It has now been found that certain non-starch and non-sugar carbon containing compositions based on mono carboxylic acids having between 2 and 5 carbon atoms, and in particular acetic acid, are capable of being used as a feedstock for the cultivation of certain oleaginous microorganisms capable of producing valuable Single Cell Oils. This unpredictable finding is made even more surprising by the fact that the feedstock in question does not sustain the growth of all oleaginous microorganisms. Furthermore, such feedstock, according to presently available results, does not appear to sustain growth of the organisms in question throughout their entire life cycle. Although the organisms germinate from spores introduced into the feedstock and develop to the hyphal stage, the organisms do not generally proceed to the stage of sporulation with the result that the feedstock in question would not appear to be capable of constituting a natural ongoing habitat for the organisms capable of sustaining successive life cycles until the carbon source is depleted. Despite the incomplete life cycle we have found that the organisms in question are capable of converting the simple chemical compounds present in the feedstock in question into high value oils and other chemical products.

It has further been found that the Fischer-Tropsch organic acid stream, which contains $C_2$ to $C_5$ mono-carboxylic acids can be used as a feedstock carbon source for the cultivation of certain oleaginous microorganisms.

OBJECT OF THE INVENTION

It is accordingly an object of the present invention to provide a method of cultivating certain SCO producing microorganisms in a new feedstock composition and to recover valuable lipids from the cultured biomass. It is a further object of the invention to provide a method of treating an effluent stream to remove certain carbon-based chemicals therefrom.

GENERAL DESCRIPTION OF THE INVENTION

According to the invention there is provided a method for producing a single cell oil containing gamma-linolenic acid characterised in that at least one microorganism of the order Mucorales is cultured in a growth medium which contains, as a carbon source material, at least one monocarboxylic acid of between 2 and 5 carbon atoms and which is substantially starch and sugar free, and recovering the oil from the resultant cultured microorganism biomass.

In one form of the invention the microorganism may be of the family Mortierellaceae, preferably of the genus Mortierella and most preferably selected from the species consisting of *Mo. isabellina, Mo. longicollis* and *Mo. ramanniana* var. *ramanniana*.

In an alternative form of the invention the microorganism is preferably of the family Mucoraceae. Thus the microorganism is preferably selected from the group consisting of the genera Actinomucor, Mucor, Rhizomucor and Rhizopus.

In this form of the invention the microorganism is most preferably selected from the group consisting of the following species of the genus Mucor, namely:

*Mu. amphibiorum*
*Mu. ardhlaengiktus*
*Mu. azygosporus*
*Mu. bainieri*
*Mu. circinelloides f. griseocyanus*
*Mu. circinelloides f. circinelloides*
*Mu. circinelloides f. janssenii*
*Mu. circinelloides f. lusitanicus*
*Mu. fragilis*
*Mu. fuscus*
*Mu. hiemalis f. hiemalis*
*Mu. minutus*
*Mu. mousanensis*
*Mu. oblongisporus*
*Mu. plumbeus*
*Mu. prayagensis*
*Mu. recurvus* var. *indicus*
*Mu. recurvus* var. *recurvus*
*Mu. rouxii*
*Mu. sinensis*
*Mu. subtilissimus*
*Mu. tuberculisporus*
*Mu. variabilis*
*Mu. variosporus*
*Mu. zychae* var. *zychae*

In the most preferred form of the invention the microorganisms may comprise *Mucor javanicus* Whemer [described in Zentbl. Bakt. Parasit Kde. Abt., 2, 6:619, 1900] which was originally isolated from "Chinese yeast" [Ragi] at Java, Indonesia. The type culture of this organism is available as *Mucor circinelloides f. circinelloides*, CBS 203.28 from the open collection of Centraalbureau voor Schimmelcultures in Baarn, Netherlands. Another most preferred organism is *Mucor rouxii* which is similarly available from CBS and which is deposited in the open collection of that culture collection under number CBS 416.77.

The organic material in the growth medium may constitute between 0,5% and 10%, but preferably between 1% and 3% of the medium.

In a particular form of the invention the growth medium may comprise the organic acid stream derived from a Fischer-Tropsch Synthesis process and may typically have the following composition on a mass/mass basis:

$CH_3COOH$—between 0,6% and 1,15%
$C_2H_5COOH$—between 0,2% and 0,4%
i-$C_3H_7COOH$—between 0,06% and 0,19%
n-$C_3H_7COOH$—between 0,09% and 0,40%
i-$C_4H_9COOH$—between 0,02% and 0,10%
n-$C_4H_9COOH$—between 0,03% and 0,05%
balance of organic compounds—between 0,02% to 0,04%
inorganic materials—less than 0,006%
water—balance to 100%

The total acid content of the medium preferably does not exceed 10 g/l.

Preferably the organic acid medium is modified to contain assimilable nutrient sources approximately in the ratio C:N:P of 100:14:4.

The nutrient mixture preferably further contains assimilable sources of potassium and sulphur, preferably in the form of sulphates, which are present approximately in the ratio C:N:P:K:S of 100:14:4:3:1

The nitrogen may be reduced to a ratio C:N of 100:2 once the organism has reached the early to middle exponential growth phase.

The assimilable nitrogen and phosphate nutrients added to the effluent are of course only necessary insofar as the medium itself if derived from an industrial process may lack such nutrients. Where required to be added the primary nutrients may generally be added in the form of ammonium hydroxide and phosphoric acid. Phosphate salts may also be added to the growth medium.

Should the medium not contain quantities of trace elements necessary to sustain growth, a suitable cocktail of such trace elements may be added to the growth medium. In this regard it has been found that a growth medium as described above and which in addition contains the elements As, Hg, Li, Mn, Cr, Cu, in quantities of less than 0,1 mg/l; the elements Cd, Co, Zn and Fe in quantities of between 0,1 and 1 mg/l; and the elements Na, Ca, Si, Cl, Pb, Ni, F in quantities of between 1 and 10 mg/l, is suitable for sustaining growth of the microorganisms in question.

In culturing the organisms the growth medium is preferably inoculated by suspending a quantity in excess of $10^4$ spores per liter of medium onto the medium. Most preferably the quantity is not in excess of $10^6$ spores per liter. The spores are preferably applied to the effluent in the form of a powdered mixture of a sugar and/or starch-based source material on which the inoculant had been cultured to the sporulation stage.

The incubation of the inoculated growth medium is preferably carried out for a period of between 40 and 120 hours at a temperature of between 20° and 32° C., most preferably at 30° C. with aeration to maintain a dissolved oxygen level of 0.5 to 3.5 mg/l and preferably about 2.0 to 2.5 mg/liter in the growth medium, until the spores had developed to a biomass of the hyphal stage in the early to middle exponential growth phase of the organism. Nitrogen supply is then reduced. The biomass is thereafter separated from the medium when the organisms have reached the stationary growth phase.

The separation of the biomass and the water after incubation may be carried out in any convenient manner, e.g. by filtration.

The separated biomass may thereafter be extracted to recover the SCO's therefrom. The extraction is preferably carried out with hexane or chloroform and the solvent fraction may thereafter be separated into its component parts by fractional distillation.

The extracted biomass residue, which is rich in protein may be used as monogastric animal fodder, e.g. chicken feed.

Where the process of the present invention is carried out for the dual purpose of producing SCO's and for removing of organic material from the Fischer-Tropsch organic acid stream, the water fraction, after removal of the biomass and hence substantially depleted of carbon-containing material, may, if necessary, be polished to remove excess phosphates and/or ammonia if the stream is to go to waste. The stream is however preferably re-circulated as diluent water.

The harvested biomass may be treated after harvesting to recover SCO's, squalene and/or chitosan therefrom.

Examples of the invention will now be described without thereby limiting the scope of the invention to the described embodiments.

EXAMPLE 1

Culturing of *Mucor javanicus* with Fischer-Tropsch organic acid water

A sample of the organic acid stream of a Fischer-Tropsch synthetiser was analysed and found to contain approximately 1,4% [m/m] mono-carboxylic acids as major ingredients in water. The acids were present in approximately the following ratio:

$CH_3COOH$—30 parts
$C_2H_5COOH$—10 parts
i-$C_3H_7COOH$—2,00 parts
n-$C_3H_7COOH$—4,00 parts
i-$C_4H_9COOH$—1,00 part
n-$C_4H_9COOH$—1,00 part.

The acid effluent also contained other so-called non-acid chemicals which were present in much smaller quantities and which collectively constituted only about 0,04% of the effluent. The acid effluent also contained about 0,006% of inorganic matter.

The sample was diluted to an acid concentration of 4000 mg/liter by the addition of water and placed in a 17 liter fermenter. The fermenter was maintained at 30° C. and inoculated with 17 g of *Mucor Javanicus* spores prepared as described in Example 2 below, each gram of the inoculant powder containing about $10^9$ spores. The following nutrients were also added to the mixture:

$MgSO_4.7H_2O$—0,765 grams
$K_2HPO_4$—1,785 grams
$NH_3(25\%)$—20 ml
$H_3PO_4(85\%)$—1,7 ml The mixture was mixed and incubated with aeration to maintain a dissolved oxygen level of 2,0 mg/liter at the above temperature for 24 hours. The aeration is preferably carried out so as to establish airlift and so that the introduced air also serves to mix the culture medium. The pH of the mixture was maintained at pH 5.8 by the addition on demand of fresh feedstock or, if necessary 5 molar NaOH. It has been found advantageous to conduct the fermentation on this combination of a fed batch, pH controlled, airlift fermentation basis. Part of the resulting biomass was separated from the fermentation broth with the aid of sieves, dried and weighed.

The dry biomass was extracted with hexane, and the hexane was removed to obtain 5,5 grams of a crude oil fraction per 100 g of dry biomass.

The crude oil fraction was analysed and found to contain inter alia $C_{16}$ and $C_{18}$ fatty acids.

The fatty acid composition of the crude oil fraction was shown by GC analysis to comprise:

25% $C_{16:0}$ [Palmitic acid]
1,7% $C_{16:1}$ [Palmitoleic acid]
2,1% $C_{18:0}$ [Stearic acid]
24,6% $C_{18:1}$ [Oleic acid]
23,6% $C_{18:2}$ [Linoleic acid]
22,9% $C_{18:3}$ [Gamma-Linolenic acid]

The oil fraction may of course be distilled to obtain the constituents separate from one another. Squalene and chitosan may also be recovered from the biomass.

EXAMPLE 2

The spores for use in inoculating the growth medium as described in Example 1 above was prepared by inoculating a starch matrix made from wheat flour with spores of *Mucor javanicus*. The inoculated material was left in a damp atmosphere for 3 days at 30° C. during which period the microorganism grew vigorously, to the substantial exclusion of other organisms, and to the stage of sporulation.

The matrix was dried and milled to a fine powder. A spore count was performed and it was found that the powder contained about $10^9$ spores per gram.

EXAMPLE 3

In order to demonstrate that the ability to convert the simple monocarboxylic acids present in the Fischer-Tropsch organic acid water [FT water] to lipids containing gamma-linolenic acid [GLA] is shared by a large number of species in the order Mucorales, a number of strains belonging to the genera Actinomucor, Mortierella, Mucor, Rhizomucor and Rhizopus were obtained from the Centraalbureau voor Schimmelcultures, Delft [The Netherlands] and maintained on YM agar slants [Van der Walt and Yarrow, 1984] at 21° C.

A loopful of spores were used to inoculate 200 ml of a culture medium in 500 ml conical flasks, after which it was incubated on a shaker [150 rpm] at 30° C. The culture medium contained 0.10 g/l Yeast extract, 0.25 g/l $MgSO_4.7H_2O$, 10.00 g/l $K_2HPO_4$, 0.62 g/l $NH_3$, 0.05 g/l $CaCl_2.2H_2O$ and 333 ml/l FT water, giving 4 g/l total acids. The pH was set at 5.8.

It was observed that some of the strains tested for growth did not grow in the medium. Of the strains investigated the 40 best performers in terms of growth were re-tested by using 100 ml culture medium in 1000 ml conical flasks. Three repetitions of each culture were performed and the cultures were harvested at three different times. It was observed that GLA production was dependent on the duration of cultivation, the concentration increasing with time to a maximum and then decreasing thereafter.

Harvesting: The cultures were harvested by filtration through Whatman No. 1 filter paper, after which the cellular material was freeze dried.

Fatty acid analyses using gas chromatography [Megabore column] [Kock et al, 1985]. To 0.12 g lyophilised fungal material in a screw-capped [teflon-lined] glass tube was added 5.0 ml of 15% KOH in 50% $CH_3OH/H_2O$. Each tube also received 30 microliters 6% lauric acid [12:0] in methanol as internal standard. The tubes were sealed and heated in a boiling waterbath for 1 hour with continuous shaking. After cooling to room temperature the contents were adjusted to pH 2 by addition of 1,5 ml 32% HCl. After addition of 30 ml 20% $BF_3/CH_3OH$ complex [Merck, Darmstadt], and flushing with $N_2$, each tube was re-sealed and heated in a boiling waterbath for 15 minutes with continuous shaking. Each reaction mixture was again cooled to room temperature, 0,25 ml saturated NaCl solution was added and the methylated fatty acids were extracted with three successive 6,0 ml aliquots of 1:4 $CHCl_3/C_6H_{14}$ [Chloroform/hexane]. The combined extracts were concentrated under a slow stream of $N_2$, the methylated fatty acids were re-dissolved in 1,8 ml $C_6H_{14}$ and transferred to a 2 ml glass vial equipped with a teflon-lined screw-cap.

Gas chromatography was carried out with a Varian 3300 gas chromatograph equipped with a FID detector. A polar Supelcowax 10 column [30 m×0.75 mm, inside diameter] and $N_2$ as carrier gas [flowrate, 5 ml/min] were used for separation.

The GLA content [mg/g lyophilised fungal material] was calculated by using the surface area of the peak from the internal standard [12:0] on the gas chromatogram as response reference.

The results of these determinations are set out in Table 1 below in which the highest observed GLA production is recorded against each of the best performing strains as well as the time at which it was harvested. Different yields were obtained at different harvesting times. The CBS number under which the various strains are available from the open collection of CBS in Baarn, Netherlands are also given in Table 1,

TABLE 1

| Species | CBS | mgGLA/g | Harvest time hours |
|---|---|---|---|
| Genus: Actinomucor | | | |
| Actinomucor elegans | 100.09 | 16.27 | 44 |
| Genus: Mortierelia | | | |
| Mo. isabellina | 208.32 | 9.97 | 168 |
| Mo. longicollis | 209.32 | 17.54 | 168 |
| Mo. ramanniana var. ramanniana | 112.08 | 11.74 | 192 |
| Mo. parvispora | 304.52 | 0.08 | 168 |
| Genus: Mucor | | | |
| Mu. amphibiorum | 763.74 | 32.99 | 48 |
| Mu. ardhlaengiktus | 210.8 | 11.52 | 52 |
| Mu. azygosporus | 292.63 | 13.18 | 168 |
| Mu. bainieri | 293.63 | 27.67 | 44 |
| Mu. circinelloides f. griseocyanus | 116.08 | 24.89 | 44 |
| Mu. circinelloides f. circinelloides | 119.08 | 30.90 | 44 |
| Mu. circinelloides f. janssenii | 232.29 | 24.32 | 44 |
| Mu. circinelloides f. circinelloides | 203.28 | 36.72 | 44 |
| Mu. circinelloides f. lustitanicus | 108.17 | 30.62 | 52 |
| Mu. fragilis | 236.35 | 24.95 | 52 |
| Mu. fuscus | 132.22 | 20.96 | 48 |
| Mu. hiemalis f. hiemalis | 110.19 | 24.33 | 48 |
| Mu. minutus | 586.67 | 26.35 | 52 |
| Mu. mousanensis | 999.7 | 23.40 | 52 |
| Mu. oblongisporus | 569.7 | 13.10 | 48 |
| Mu. plumbeus | 111.07 | 18.85 | 96 |
| Mu. prayagensis | 816.7 | 27.78 | 48 |
| Mu. recurvus v. indicus | 786.7 | 33.63 | 48 |
| Mu. recurvus var. recurvus | 317.52 | 7.09 | 44 |
| Mu. rouxii | 416.77 | 40.20 | 48 |
| Mu. sinensis | 204.74 | 0.73 | 52 |
| Mu. subtilissimus | 735.7 | 31.93 | 96 |
| Mu. tuberculisporus | 562.66 | 18.41 | 144 |
| Mu. variabilis | 564.66 | 33.26 | 44 |
| Mu. varioporus | 837.7 | 33.42 | 48 |
| Mu. zychae var. zychae | 416.67 | 17.71 | 72 |
| Genus: Rhizomucor | | | |
| Rhizomucor miehei | 182.67 | 11.53 | 48 |
| Rhizomucor pusillus | 354.68 | 4.50 | 96 |
| Genus: Rhizopus | | | |
| Rhizopus homothallicus | 336.62 | 19.88 | 192 |
| Rhizopus microsporus var. chinensis | 631.82 | 13.34 | 44 |
| Rhizopus microsporus var. microspor. | 699.68 | 11.77 | 48 |
| Rhizopus microsporus var. rhizopodiformis | 536.8 | 11.61 | 48 |
| Rhizopus oryzae | 112.07 | 10.27 | 44 |
| Rhizopus stolonifer var. reflexus | 319.35 | 16.33 | 96 |
| Rhizopus stoloniter var. stolonifer | 609.82 | 17.24 | 72 |

EXAMPLE 4

Preparation of Inoculant of Oleaginous Microorganisms

An alternative method to the one described in Example 2 for the preparation of an inoculant of the organisms referred to Example 3 was developed.

Sabouraud agar was placed in Roux flasks [or pencillin in flasks] and inoculated with the organism to be grown by washing the organism from cultures grown in petri dishes with 10 ml phosphate buffer. The wash was spread over the Sabouraud agar in the Roux flasks whereafter the flasks were incubated for 2 to 5 days at 30° C. under forced, moist and sterile air introduced into the flasks. The resultant growth was washed from the flasks with phosphate buffer with 0,2% Tween 80 and used as inoculant.

EXAMPLE 5

Cultivation of M. javanicus on Acetic Acid as carbon source

To further demonstrate the ability of Mucor circinelloides f. circinelloides [CBS 203.28] [also referred to by the trivial name M. javanicus] to assimilate acetic acid as carbon source in the production of GLA a growth medium was prepared as follows:

| | |
|---|---|
| $H_2O$ | 4 liters |
| Citric Acid | 0.5 g |
| $NH_4Cl$ | 3.2 g |
| $MgSO_4.7H_2O$ | 1.6 g |
| $KH_2PO_4$ | 6.0 g |
| $CaCl_2.2H_2O$ | 0.1 g |
| Yeast Extract | 2.0 g |
| Acetic Acid | 8.0 g | pH was set to 5.5 with KOH.

The following ingredients were added as trace elements:

| | |
|---|---|
| $FeSO_4.7H_2O$ | 0.01 g/L |
| $ZnSO_4.7H_2O$ | 0.01 g/L |
| $MnSO_4.4H_2O$ | 0.001 g/L |
| $CuSO_4.5H_2O$ | 0.0005 g/L |

4 Liters of the medium was placed in 5 liter fermenters and inoculated with 400 ml [i.e. 10%] inoculum prepared over a growth period of 24 hours in vortex aerated bottles stirred at 600 r.p.m. at 30° C. The composition of the inoculum medium was as follows:

| | |
|---|---|
| $H_2O$ | 800 ml |
| Glucose | 24 g |
| $KH_2PO_4$ | 5.6 g |
| $Na_2HPO_4$ | 1.6 g |
| $MgSO_4.7H_2O$ | 1.2 g |
| Yeast Extract | 1.2 g |
| $CaCl_2.2H_2O$ | 0.08 g |
| Sodium glutamate | 2.4 g |

All media were autoclaved.
The growth conditions in the 5 liter fermenter were as follows:

| | |
|---|---|
| pH | 5.5 |
| Stirring rate | 700 rpm |
| Temperature | 30° C. |
| Aeration | 0.5 vvm |
| Antifoam | A small amount [3 drops] added at start of fermentation run |

50% acetic acid was added to the medium from a supply reservoir to keep the pH at 5,5 during the growth period.

The acetic acid utilisation was determined according to the volume of acetic acid used from the supply reservoir and volume of culture in the fermenter.

The increase of biomass over time, the lipid content as a percentage of biomass and the gamma linolenic acid content of the fatty acids produced were determined. The results are set out in Table 2.

TABLE 2

| Cultivation of Mucor javanicus with Acetic Acid | | | | | |
|---|---|---|---|---|---|
| Time [hrs] | Biomass $[gL^{-1}]$ | Resid. $N_2$ $[NH_4^+]$ | Acetic acid utilised [ml/L] | Lipid % Biomass | % GLA of F.A. |
| 0 | 0.1 | | | | |
| 13 | 2.4 | Depleted | | | |
| 20 | 4.1 | — | 9.4 | 18.2 | 13.9 |
| 37 | 6.0 | — | 20.1 | 21.0 | 16.2 |
| 44 | 6.2 | — | 23.1 | 20.0 | 15.6 |
| 61 | 5.4 | — | 28.1 | 21.5 | 15.7 |
| 68 | 6.9 | — | — | 21.6 | 15.4 |
| 85 | 7.8 | 29,0 | 31.9 | 19.5 | 16.0 |

It is believed that the nutritional stress under which the organism was placed due to the fact that the nitrogen in the medium was depleted within 13 hours contributed to the high GLA production. By the process of the invention the acetic acid, which is toxic to the organisms at levels in excess of about 10–20 g/l is slowly titrated into the culture medium such that the total acid content remains below toxic levels. It will be seen that by this procedure the organisms utilised a total of 31,9 ml/l acetic acid.

EXAMPLE 6

The performance of Mucor javanicus [i.e. Mucor circinelloides f. circinelloides] in the production of GLA from glucose as a carbon source material was compared with its performance when acetic acid is used as carbon source material. The strain used in this experiment was not the same as the one used in the experiment of Example 5 but is also available from the open collection of CBS in Baarn, Netherlands under number CBS 108.16.

A 5 liter fermenter was provided with 4 liters of a glucose-based growth medium of the following composition in water.

| | |
|---|---|
| Glucose | 50 $gL^{-1}$ |
| $(NH_4)_2SO_4$ | 1.7 $gL^{-1}$ |
| $KH_2PO_4$ | 2.0 $gL^{-1}$ |
| $MgSO_4.7H_2O$ | 0.5 $gL^{-1}$ |
| $CaCl_2.2H_2O$ | 0.2 $gL^{-1}$ |
| $FeSO_4.7H_2O$ | 0.01 $gL^{-1}$ |
| $ZnSO_4.7H_2O$ | 0.01 $gL^{-1}$ |
| $MnSO_4.4H_2O$ | 0.001 $gL^{-1}$ |
| $CuSO_4.5H_2O$ | 0.0005 $gL^{-1}$ |
| Yeast Extract | 1 $gL^{-1}$ |

The pH of the medium was set at 5,5 with KOH.

400 ml of an inoculum containing Mucor javanicus strain CBS 108.16 in an inoculum medium of the same composition and prepared as described in Example 5 was used to inoculate the above growth medium. The growth conditions were also the same as described in Example 5.

In the comparative trial a 5 liter fermenter was provided with 4 liters of an acetic acid based growth medium of the following composition:

| | |
|---|---|
| $H_2O$ | 4 L |
| Citric Acid | 0,5 g |
| $NH_4Cl$ | 5,52 g |
| $MgSO_4.7H_2O$ | 1,6 g |
| $KH_2PO_4$ | 6,0 g |
| $CaCl_2.2H_2O$ | 0,1 g |
| Yeast Extract | 4,0 g |
| Acetic Acid | 20,0 g |

Trace elements in the quantities listed in Example 5 were also added to the growth medium.

The medium was inoculated with 400 ml of the inoculum containing M. javanicus [CBS 108.16] as described above. The growth conditions were the same as for the glucose-based growth medium. However, throughout the growth period a solution of 50% [v/v] acetic acid in water was slowly titrated from a reservoir into the growth medium to maintain the pH of the growth medium at 5,5. In this manner it was ensured that the acetic acid content of the growth medium remained at a sublethal [i.e. non-toxic] level of 5 g/l. The cultivation was carried on in this manner for a period of 162 hours and during this period the acetic acid utilisation, determined according to the volume of acetic acid used from the reservoir and the volume of culture in the fermenter, was determined to have been 81,4 ml/L which quantity would have been toxic to the organism if originally present in the fermenter.

Various determinations were made in comparing the performance of the microorganism on the two culture media. The results are set out in Table 3.

TABLE 3

| Comparison of performance of M. javanicus in GLUCOSE and ACETIC ACID | | |
|---|---|---|
| Parameters | Glucose 50 g/L | Acetic Acid 5 g/L |
| Total Lipid Content of mold [% w/w] | 22.7 [72 h] | 22.6 [92 h] |
| Total Neutral Lipid [NL] fraction [% w/w] | 20.4 [72 h] | 18.1 [92 h] |
| GLA % of total F.A. in NL-fraction | 15.1 [72 h] | 13.9 [92 h] |
| GLA content of mold [NL-fraction] [% w/w] | 3.1 | 2.5 |
| Biomass Density After 40 h | 12.0 | 11.4 |

TABLE 3-continued
Comparison of performance of M. javanicus in GLUCOSE and ACETIC ACID

| Parameters | | Glucose 50 g/L | Acetic Acid 5 g/L |
|---|---|---|---|
| [g dw/L] | After 70 h | 16.6 | 14.4 |
| | After 85 h | 16.5 | 15.4 |
| Biomass Yield | After 40 h | 0.30 | 0.36+ |
| [g dw/source* util.] | After 70 h | 0.33 | 0.29 |
| | After 85 h | 0.33 | 0.28 |
| GLA-Yield | After 40 h | 0.010 | 0.007+ |
| [g GLA/source* util.] | After 70 h | 0.012 | 0.007 |
| | After 85 h | 0.012 | 0.009 |
| Production Time [h] | | 92 | 162 |
| Lipid Yield [g lipid/ | After 40 h | 0.07 | 0.07+ |
| source* util.] | After 70 h | 0.08 | 0.06 |
| | After 85 h | 0.07 | 0.06 |
| Lipid Content | After 40 h | 2.9 | 2.3+ |
| [g/L] | After 70 h | 3.8 | 3.0 |
| [% Lipid × 7] | After 85 h | 3.6 | 3.4 |
| GLA Content | After 40 h | 0.41 | 0.24+ |
| [g/L] | After 70 h | 0.57 | 0.33 |
| [% GLA × 12] | After 85 h | 0.57 | 0.45 |
| GLA Content | After 40 h | 34.2 | 19.2+ |
| [mg/g dw] | After 70 h | 34.3 | 23.0 |
| [13/7] | After 85 h | 34.5 | 29.0 |

Notes:
*Total source utilised excludes ca.12 g glucose from inoculum [12 g glucose/400 ml medium added as 10% inoculum]. Values indicate grams glucose utilised in fermenter medium and ml acetic acid utilised for acetic acid based medium.
F.A. fatty acid
dw dry weight
+Samples taken after 44 h
All data were read from graphs and are rounded off The methods followed in the determinations set out above were as follows:

Dry weight determination. Culture biomass was determined by filtration of 2 ml of culture through a pre-weighed membrane filter [GF/B, Whatman], washed with distilled water [6×2 ml] and dried to a constant weight at 110° C. This procedure was performed in duplicate.

Lipid extraction. This was performed on freeze-dried material as described by Kendrick & Ratledge [1992] and include extraction with chloroform/methanol [2:1, v/v] as described by Folch et al. [1957], three washes with distilled water and final evaporation of the organic phase. Lipid material was finally dissolved in a minimal volume of diethyl ether and transferred to pre-weighed vials. For determination of lipid weights, samples were dried to constant weight in a vacuum oven at 50° C., over $P_2O_5$.

Fractionation of extracted lipid. Extracted lipid was dissolved in chloroform and applied to a column [140 mm×20 mm] of activated [by heating overnight at 110° C.] silicic acid. Neutral-, sphingo- and glyco-lipids [as a combined fraction], as well as polar lipids, were eluted by successive applications of organic solvents as described by Kendrick & Ratledge [1992]. Final solvent removal and storage was as for whole lipid extracts. Each fraction was then purified further by thin layer chromatography.

Thin-layer chromatography. Thin-layer chromatography of the neutral-, sphingo- and glyco-lipid fraction was on silica gel thin-layer plates backed with aluminium [Merck]. The polar fraction, containing phospholipids, was separated using chloroform/methanol/water/acetic acid [65:43:3:1 by vol.].

The neutral lipid fraction was separated using petroleum ether [60° to 80° C.]/diethyl ether/acetic acid [85:15:1, by vol.]. The combined sphingo- and glyco-lipid fraction was separated using chloroform/methanol/$NH_4OH$, sp. gr. 0,880, [80:20:0,2, by vol.]. Plates were developed one dimensionally by the ascending technique and visualised by exposure to $I_2$ vapour. Phospholipids were further visualised by staining with Dragendorff reagent, which specifically stains choline containing lipids, ninhydrin for the detection of lipids with free amino groups [Higgins, 1987] and a molybdenum blue reagent spray for the detection of phospholipids in general by staining phosphate-containing lipids [Dittmer & Lester, 1964]. Glyco-lipids were visualised by spraying with alphanaphthol solution [Higgins, 1987]. Further identification was achieved by running suitable authentic standards alongside experimental samples.

Fatty acid analysis. Lipid was dissolved in chloroform and methylated by the addition of trimethyl sulphonium hydroxide [TMSH] as described by Butte [1983].

The FAME were analysed using a Phillips PU 4500 gas chromatograph and a 10% diethylene glycol succinate column [2 m×4 mm] as described by Kendrick & Ratledge [1992]. Identification of peaks was by reference to authentic standards.

Glucose analysis. Glucose was analysed by the GOD-PERID Test [Boehringer Mannheim].

Nitrogen analysis. Performed by estimating ammonia by the indophenol method [Chaney, A. L. and Marbach, E. P. (1962) Clinical Chemistry 8, 130].

From the results set out in Table 3 it will be seen that the performance of M. javanicus [CBS 108.16] on glucose was virtually the same as on acetic acid employed in the manner described herein. This is a most unexpected result.

The references referred to in the above examples are as follows:

Butte, W. (1983). Rapid method for the determination of fatty acid profiles from fats and oils using trimethylsulphonium hydroxide for transesterification. Journal of Chromatography 261, 142–145.

Dittmer, J. C. & Lester, L. (1964). A simple specific spray for the detection of phospholipids on thin-layer chromatograms. Journal of Lipid Research 5, 126.

Folch, J., Lees, M. & Sloane-Stanley, G. H. (1957). A simple method for the isolation and purification of total lipids from animal tissues. Journal of Biological Chemistry 226, 497–509.

Higgins, J. A. (1987). Separation and analysis of membrane lipid components, In Biological membranes—a practical approach, pp. 103–137. Edited by J. B. C. Findlay & W. H. Evans. Washington D.C.: IRL Press.

Kendrick, A. J. & Ratledge, C. (1992). Lipids of selected molds grown for production of n-3 and n-6 polyunsaturated fatty acids. Lipids 27, 15–20.

Kock, J. L. F. Botes, P. J., Erasmus, S. C., and Lategan, P. M. (1985). A rapid method to differentiate between four species of the Endomycetaceae. Short Comm. J. Gen. Microbiol. 131: 3393–3396.

Many variations of the invention may be devised without departing from the spirit of the invention. Thus the fermentation process may be carried out in a continuous process.

We claim:

1. A method for producing a single cell oil which contains gamma-linolenic acid from a monocarboxylic acid of 2 to 5 carbon atoms as carbon source material, said method comprising the steps of:

culturing at least one microorganism of the order Mucorales and belonging to a genus selected from the group consisting of Mortierella, Actinomucor, Mucor, Rhizomucor and Rhizopus in a growth medium, the carbon source material of said growth medium consisting essentially of at least one monocarboxylic acid of 2 to 5 carbon atoms in a quantity such that the concentration of the acid is sub-lethal to the organism, wherein said microorganism utilizes said monocarboxylic acid as a carbon source and thereby produces said oil;

wherein the growth medium is replenished during said culturing with said monocarboxylic acid in response to consumption of said monocarboxylic acid by the microorganism; and recovering the oil from the resultant cultured microorganism biomass.

2. The method of claim 1, wherein the microorganism is a species selected from the group consisting of *Mo. isabellina*, *Mo. longicollis* and *Mo. ramanniana* var *ramanniana*.

3. The method of claim 1, wherein the microorganism belongs to the genus Mucor and is a species selected from the group consisting of:

*Mu. amphibiorum,*
*Mu. ardhlaengiktus,*
*Mu. azygosporus,*
*Mu. bainieri,*
*Mu. circinelloides f. griseocyanus,*
*Mu. circinelloides f. circinelloides,*
*Mu. circinelloides f. janssenii,*
*Mu. circinelloides f. lusitanicus,*
*Mu. fragilis,*
*Mu. fuscus,*
*Mu. hiemalis f. hiemalis,*
*Mu. minutus,*
*Mu. mousanensis,*
*Mu. oblongisporus,*
*Mu. plumbeus,*
*Mu. prayagensis,*
*Mu. recurvus* var. *indicus,*
*Mu. recurvus* var. *recurvus,*
*Mu. rouxii,*
*Mu. sinensis,*
*Mu. subtilissimus,*
*Mu. tuberculisporus,*
*Mu. variabilis,*
*Mu. variosporus,* and
*Mu. zychae* var. *zychae.*

4. The method of claim 1, wherein the growth medium comprises a mixture of acetic acid assimilable sources of nitrogen and phosphate.

5. The method of claim 4, wherein the growth medium also includes at least one acid selected from the group consisting of propanoic acid, butanoic acid, isobutyric acid, n-valeric acid and i-valeric acid and also assimilable sources of potassium and sulphur and trace elements required to sustain the growth of microorganisms.

6. The method of claim 1, wherein the carbon source material is the aqueous organic acid stream derived from a Fischer-Tropsch process.

7. The method of claim 1, wherein the total organic acid content of the culture medium is maintained at less than 10 g/l by addition of the acid on demand as the acid is consumed by the organisms.

8. The method of claim 7, wherein the total organic acid content of the culture medium is maintained at between 1 and 5 g/l.

9. A method of reducing the mono-carboxylic acid content of the aqueous organic acid stream of the Fischer-Tropsch process, said method comprising the steps of:

introducing said aqueous organic acid stream into a culture medium containing a microorganism of the order Mucorales and belonging to a genus selected from the group consisting of Mortierella, Actinomucor, Mucor, Rhizomucor and Rhizopus;

cultivating said microorganism under conditions such that the concentration of said monocarboxylic acid present in the growth medium is sub-lethal to said microorganism, and under conditions such that said microorganism utilizes said monocarboxylic acid as a carbon source; and separating the biomass resulting from such cultivation from the growth medium.

* * * * *